US009603685B2

(12) United States Patent
Eatherton

(10) Patent No.: US 9,603,685 B2
(45) Date of Patent: Mar. 28, 2017

(54) METHOD OF MANUFACTURING AN INTERDENTAL CLEANER

(71) Applicant: LeedTech Resources Company, Naperville, IL (US)

(72) Inventor: Dennis Eatherton, Deer Park, IL (US)

(73) Assignee: LeedTech Resources Company, LLC, Naperville, IL (US)

( * ) Notice: Subject to any disclaimer, the term of this patent is extended or adjusted under 35 U.S.C. 154(b) by 160 days.

(21) Appl. No.: 14/022,012

(22) Filed: Sep. 9, 2013

(65) Prior Publication Data

US 2014/0008837 A1  Jan. 9, 2014

(51) Int. Cl.
| | |
|---|---|
| *A61C 15/02* | (2006.01) |
| *A46B 1/00* | (2006.01) |
| *A46B 15/00* | (2006.01) |
| *A46D 1/00* | (2006.01) |
| *A46D 3/00* | (2006.01) |
| *B29C 45/16* | (2006.01) |
| *B29L 31/42* | (2006.01) |

(52) U.S. Cl.
CPC .............. *A61C 15/02* (2013.01); *A46B 1/00* (2013.01); *A46B 15/0093* (2013.01); *A46D 1/0207* (2013.01); *A46D 3/00* (2013.01); *B29C 45/1671* (2013.01); *B29C 45/1676* (2013.01); *A46B 2200/108* (2013.01); *B29C 2045/1678* (2013.01); *B29L 2031/42* (2013.01); *B29L 2031/425* (2013.01)

(58) Field of Classification Search
CPC .............. A61C 15/02; A61C 15/0093; B29C 2045/1678; B29C 2031/42; B29C 45/1671; B29C 45/1676

USPC ................... 264/243, 328.1, 297.2; 425/543
See application file for complete search history.

(56) References Cited

U.S. PATENT DOCUMENTS

| | | | |
|---|---|---|---|
| 2,359,840 A * | 10/1944 | Goessling | 425/146 |
| 3,775,848 A | 12/1973 | Barnett | |
| 3,978,182 A | 8/1976 | Luthra | |
| 5,223,275 A * | 6/1993 | Gellert | 425/130 |
| 6,065,176 A * | 5/2000 | Watanabe | A46B 9/045 15/167.1 |
| 6,158,444 A | 12/2000 | Weihrauch | |
| 7,534,103 B2 * | 5/2009 | Weyand et al. | 425/543 |
| 7,632,489 B2 * | 12/2009 | Wyatt | A46B 1/00 132/208 |
| 8,042,217 B2 * | 10/2011 | Sorrentino | A46B 9/026 15/167.1 |
| 8,082,887 B2 * | 12/2011 | Fernandez | A01K 13/002 119/612 |
| 8,523,888 B2 * | 9/2013 | Gatzemeyer | A46B 15/0055 15/110 |
| 8,663,520 B2 * | 3/2014 | Kalbfeld et al. | 264/138 |
| 2003/0044604 A1 * | 3/2003 | Weihrauch | A46B 15/001 428/373 |
| 2003/0163884 A1 * | 9/2003 | Weihrauch | A46B 3/22 15/207.2 |
| 2005/0172439 A1 * | 8/2005 | Weihrauch | 15/187 |

(Continued)

*Primary Examiner* — Nahida Sultana

(57) ABSTRACT

An elongated core comprising a nylon or polypropylene is extruded. An interdental cleaner portion, comprising fingers, is injection molded about a first portion of the core. The interdental cleaner portion has thermoplastic elastomer. A handle portion is injection molded about a second portion of the core. The handle portion has polypropylene.

15 Claims, 7 Drawing Sheets

(56) References Cited

U.S. PATENT DOCUMENTS

| | | | | |
|---|---|---|---|---|
| 2006/0165473 A1* | 7/2006 | Hohlbein | ............. | A46B 5/0062 |
| | | | | 401/132 |
| 2008/0044791 A1* | 2/2008 | Tsurukawa | ........... | A46B 5/0075 |
| | | | | 433/141 |
| 2010/0125960 A1* | 5/2010 | Schamberg | .......... | A46B 5/0062 |
| | | | | 15/143.1 |
| 2011/0099735 A1* | 5/2011 | Stadeker | .................... | 15/104.94 |
| 2013/0291320 A1* | 11/2013 | Kirchhofer et al. | ........... | 15/22.1 |
| 2014/0090192 A1* | 4/2014 | Amron | ............... | A46B 15/0067 |
| | | | | 15/22.1 |
| 2014/0137353 A1* | 5/2014 | Wen et al. | ................... | 15/167.1 |
| 2014/0137354 A1* | 5/2014 | Newman et al. | ............ | 15/167.1 |
| 2016/0120298 A1* | 5/2016 | Grewal | ................... | A46B 3/04 |
| | | | | 15/167.1 |
| 2016/0135932 A1* | 5/2016 | Butz | ...................... | A61C 15/02 |
| | | | | 132/329 |

* cited by examiner

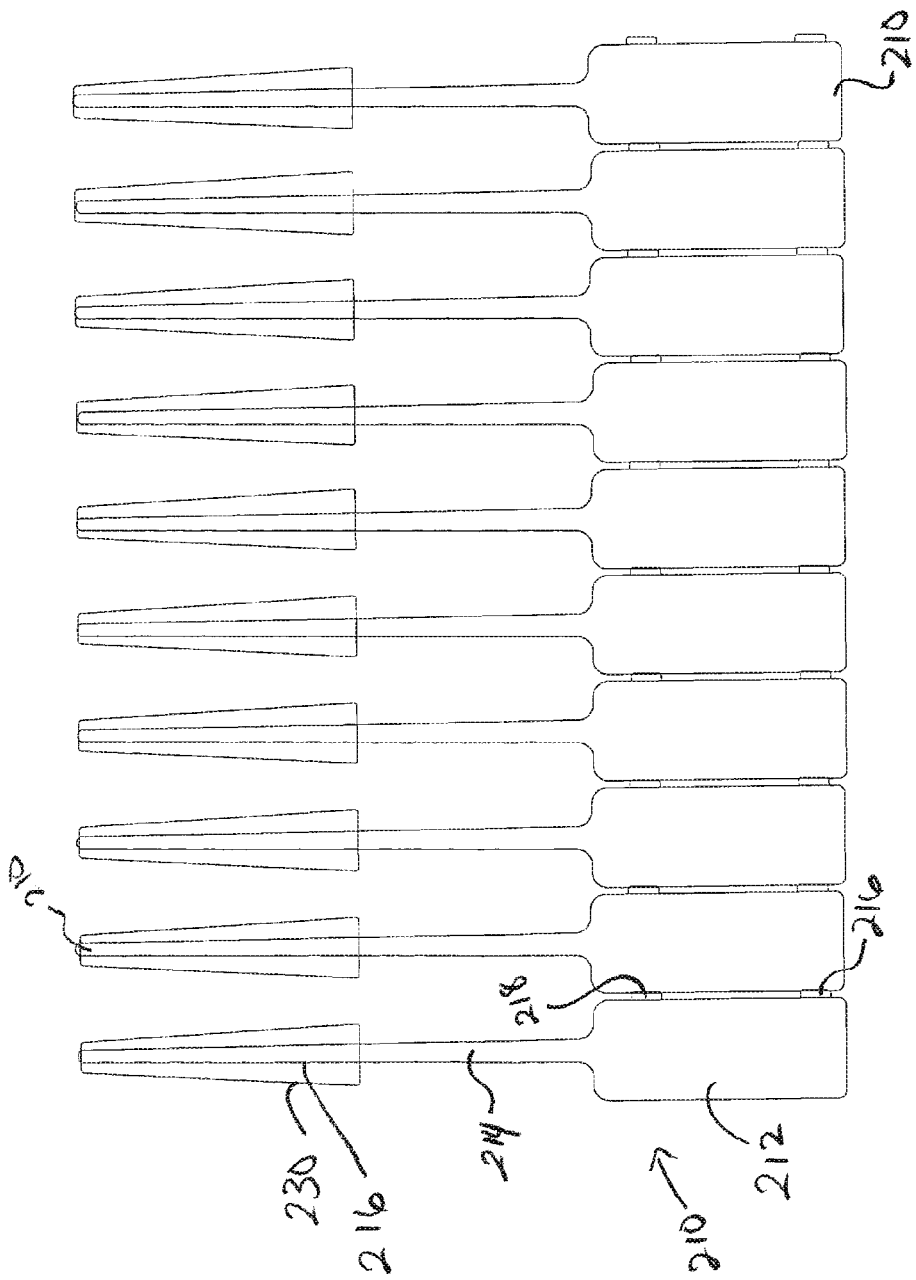
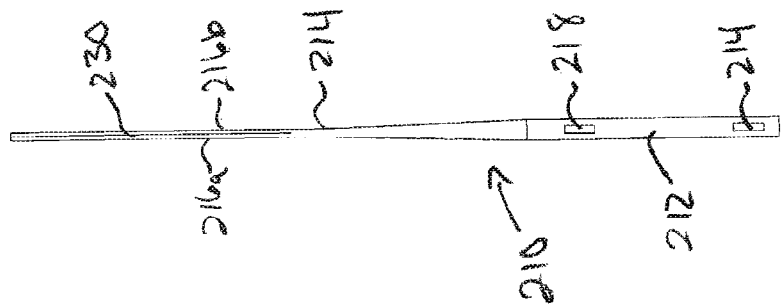

METHOD OF MANUFACTURING AN INTERDENTAL CLEANER

FIELD OF THE INVENTION

This invention relates in general to interdental cleaners.

BACKGROUND OF THE INVENTION

It is known that it is important to clean the interdental spaces to maintain healthy teeth and gums. Further, it is known that the lack of cleaning of interdental spaces can lead to diseases such as periodontosis. Tooth brushes general do not sufficiently clean the interdental spaces.

Dental floss is known for cleaning interdental spaces. However, there are drawbacks to the use of floss, such as the difficulty handling by the user, and the need for proper use for receiving beneficial effects. It is also know in the art to use an interdental brushes and toothpicks to clean interdental spaces.

The present inventor recognized the need for an improved manufacturing process for making an interdental cleaner that reduces the complexity of the manufacturing process and reduces costs. The present inventor recognized the need for an improved interdental cleaner manufacturing process that result in a strong yet semi flexible device that can penetrate the interdental spaces and provide the needed cleaning therein while not overly aggravating the adjacent gum tissue.

SUMMARY OF THE INVENTION

Methods of manufacturing an interdental cleaner are disclosed. An elongated core comprising a nylon or polypropylene is extruded. An interdental cleaner portion, comprising fingers, is injection molded about a first portion of the core. The interdental cleaner portion comprises thermoplastic elastomer. A handle portion is injection molded about a second portion of the core. The handle portion comprises polypropylene.

In another embodiment of a method of manufacturing an interdental cleaner, a strip of cleaner material is placed in an injection molding machine. A plurality of interdental cleaner bodies are injection molded about the strip of cleaner material. The strip is cut about each cleaner body to form a cleaner element portion joined with the cleaner body.

Numerous other advantages and features of the present invention will be become readily apparent from the following detailed description of the invention and the embodiments thereof, from the claims, and from the accompanying drawings.

BRIEF DESCRIPTION OF THE DRAWINGS

FIG. 7 is a front view of the plurality of second embodiment interdental cleaners at a later stage of manufacturing from that shown in FIG. 6.

FIG. 8 is a right side view of one of the second embodiment interdental cleaner from FIG. 7.

DETAILED DESCRIPTION

Figure 1:
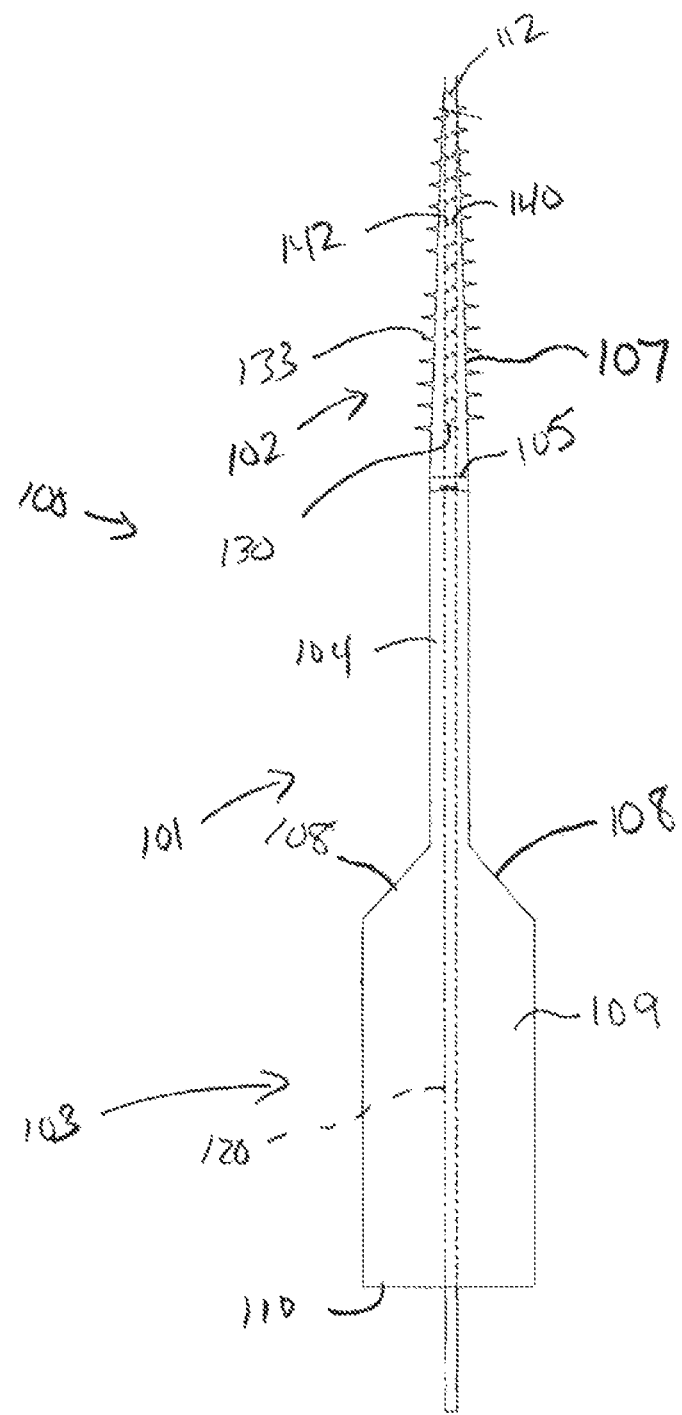
FIG. 1 is a front view of an interdental cleaner of the invention.
Figure 2:
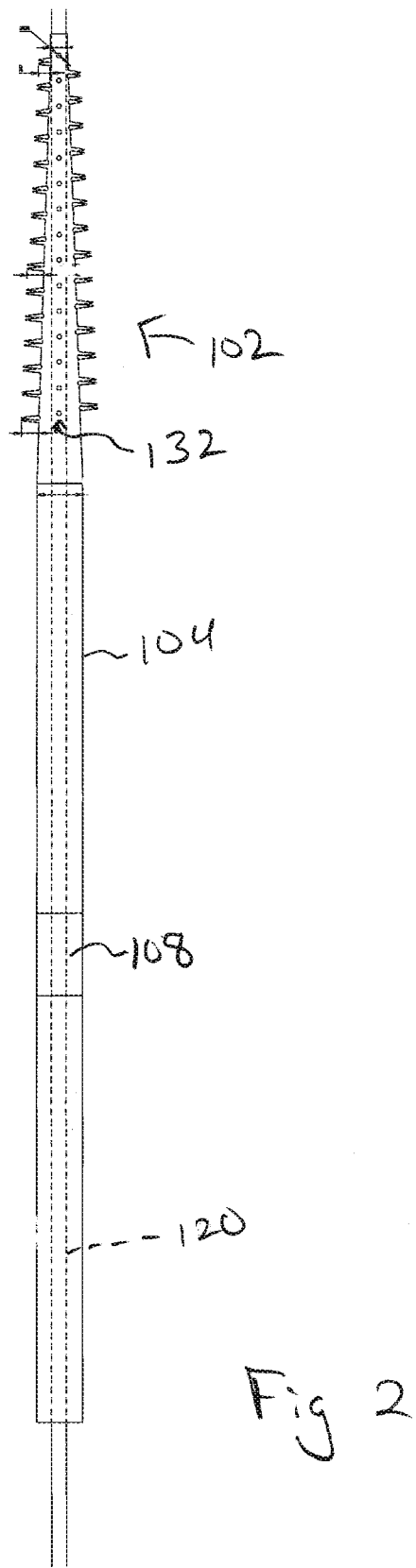
FIG. 2 is a side view of the interdental cleaner of FIG. 1.

Methods of manufacturing interdental cleaners are disclosed. The following description is presented to enable any person skilled in the art to make and use the invention. For the purposes of explanation, specific nomenclature is set forth to provide a plural understanding of the present invention. While this invention is susceptible of embodiment in many different forms, there are shown in the drawings, and will be described herein in detail, specific embodiments thereof with the understanding that the present disclosure is to be considered as an exemplification of the principles of the invention and is not intended to limit the invention to the specific embodiments illustrated.

FIG. 1-5 shows a first embodiment interdental cleaner 100. The cleaner 100 comprises a body 101 and a core 120 extending through the body. The core is rigid and provides support to the body. The body comprises a handle section 103, an intermediate section 104, and an interdental section 102. The body is softer and more flexible than the core which prevents overly aggravating the gum tissue during proper use.

Figure 3:
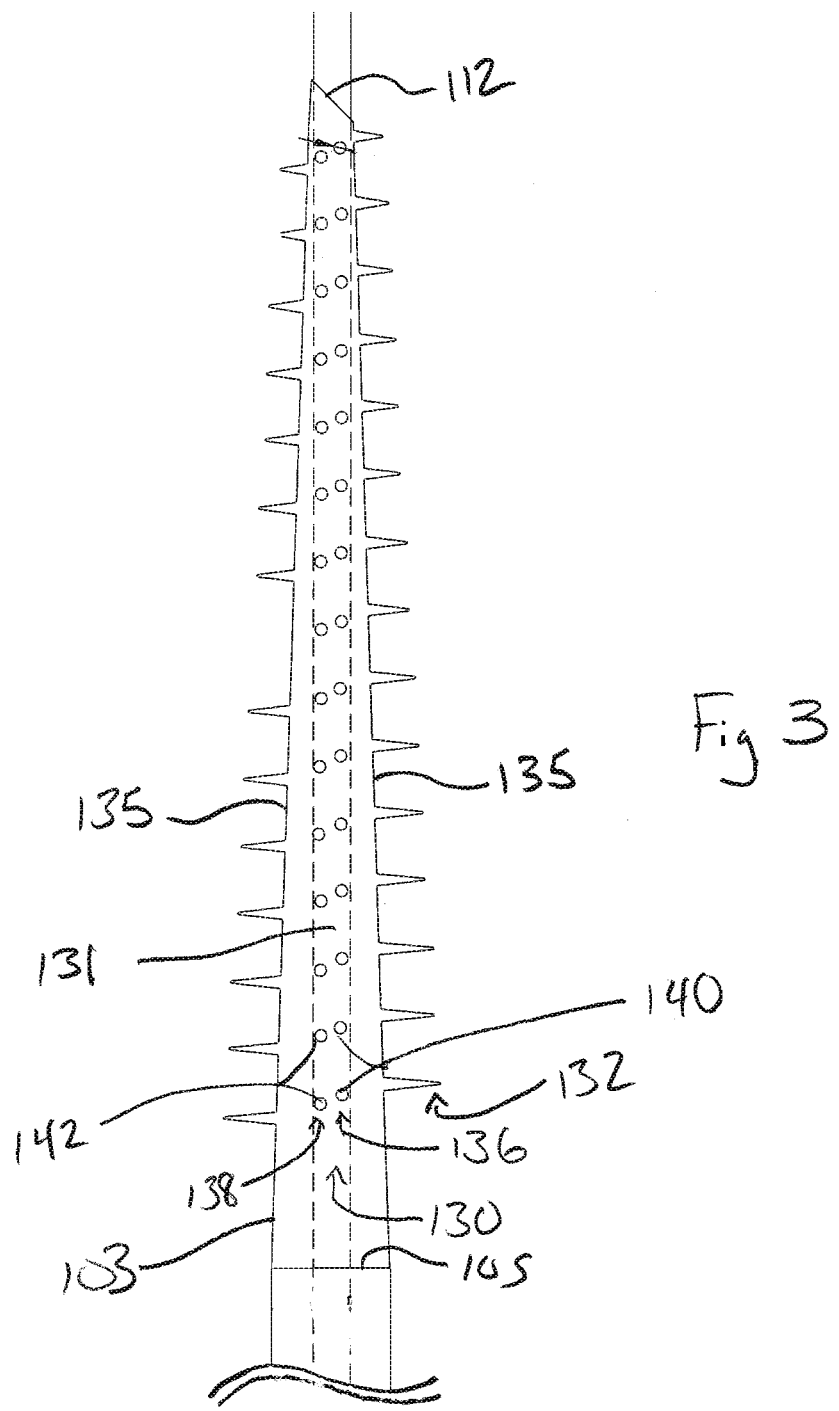
FIG. 3 is an enlarged front view of a portion of the interdental cleaner taken from FIG. 1.

The interdental section 102 comprises a plurality of fingers 133, 140, 142. A shaft 107 of the interdental section 102 is tapered from an intersection 105 with the intermediate section 104 toward a proximal end 112. The proximal end 112 may be tapered as shown in FIG. 3. Each side of a first pair of opposite sides 135 of the interdental section comprise one row 132 of fingers 133. Each side of a second pair of opposite sides 131 of the interdental section comprise a double row 136,138 of fingers 140, 142. The shaft 107 maybe conical in shape so that the sides 131, 135 are continuously curved in the lateral directions and tapering in the longitudinal directions. The shaft may have other cross-sectional shapes, such as square, rectangle, triangle, etc.

Figure 4:
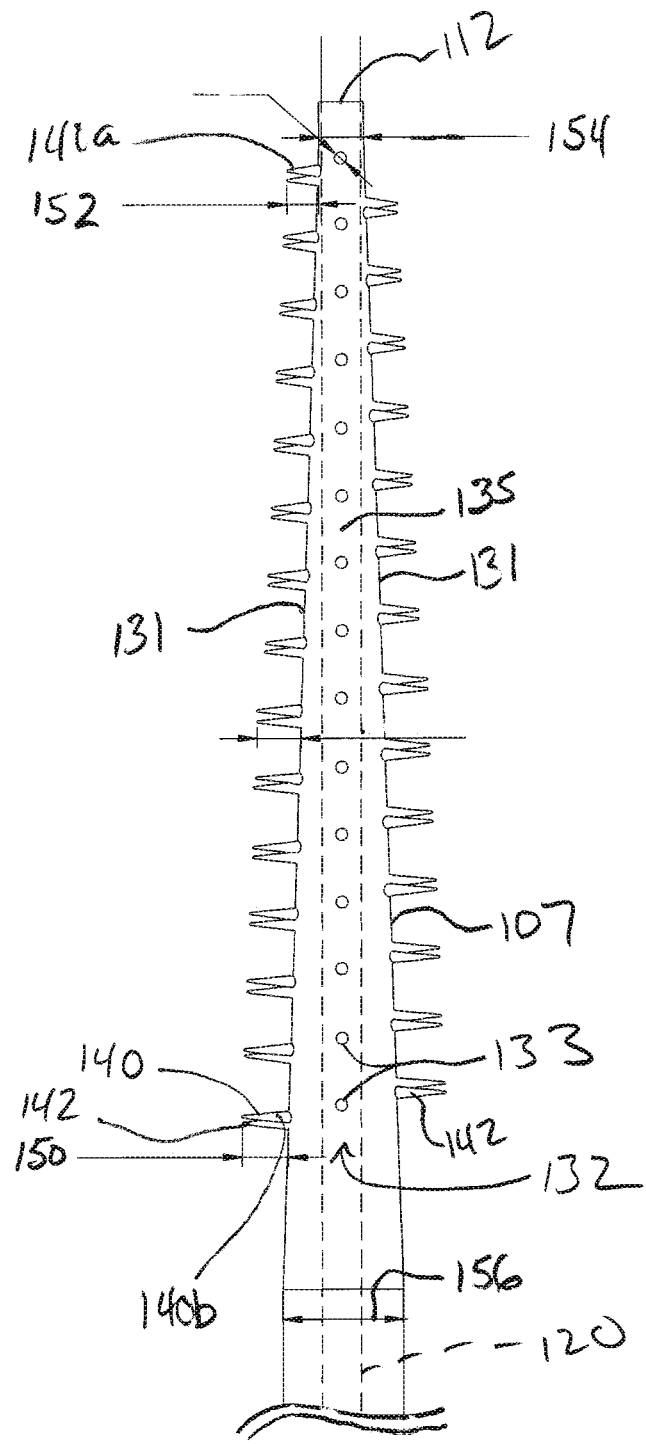
FIG. 4 is an enlarged side view of a portion of the interdental cleaner taken from FIG. 2.
Figure 5:
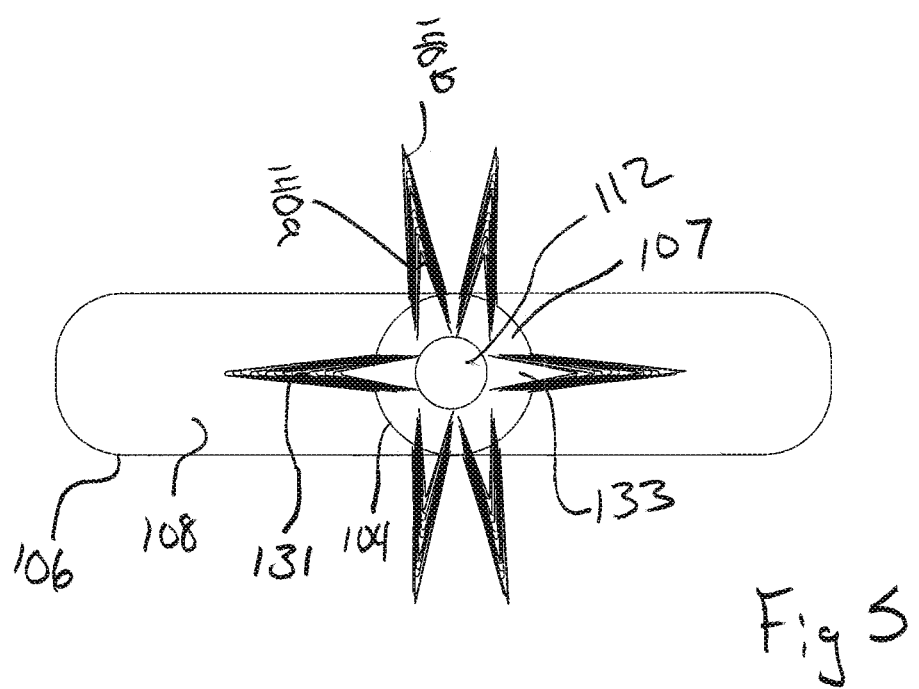
FIG. 5 is a top view of the interdental cleaner of FIG. 1.

The fingers 140 of row 136 are vertically offset from the adjacent fingers 142 of row 138, as shown, in particular in FIGS. 3 and 4. The fingers 133 of row 132 are vertically offset from the adjacent fingers 140, 142 on opposite sides of the fingers 133. Therefore, as shown in FIG. 4, bottom finger 140 (on the left side of FIG. 4) is vertically offset lower from the bottom finger 133, and the bottom finger 142 (on the right side of FIG. 4) is vertically offset higher from the bottom finger 133.

In one embodiment, the length 150 of the fingers 142, 140, 133 increases by 0.02 millimeters (mm) per finger in the same row progressing downward from the proximal end, so that if the bottom the top most finger 140a has a length 152 of 0.34 mm then the bottom most finger 140b will have a length 150 of 0.62 mm. In one embodiment, the distance between each finger in a row is 0.90 mm and the diameter of the finger at the location where the finger joins to or into the shaft 107 is 0.16 mm. In one embodiment, as shown in FIG. 4, the shaft 107 has a diameter 154 of 0.60 mm adjacent the proximal end 112 and a diameter of 1.63 mm at the point of intersection with the intermediate section 104. The intermediate section has a constant diameter 156 throughout its length.

The handle 103 has a main body 109, a distal end 110, and a handle proximal end 108 that joins or is formed with the intermediate section 104. The handle proximal end has opposite tapered surfaces that extend inward toward the proximal end 112 until the intermediate section. The handle section is configured to increase the ease for a user to grip the interdental cleaner.

A manufacturing process for making the interdental cleaner 100 is also disclosed. First the core 120 is extruded from an extruding machine. The core can comprise nylon or polypropylene.

The extruding step comprises heating and melting nylon or polypropylene so that the nylon or polypropylene is a flowable material. Next the flowable material is fed into a die having an inlet opening at a first end and an outlet opening at an opposite second end. The outlet opening is circular in shape, but can be other shapes, such as square, rectangle, quadrilateral, triangle, etc. Then the process of feeding or pushing the flowable material into the die causes the flowable material to be extruded from the outlet of the die, having a cross-sectional shape corresponding to the shape of the die outlet opening. The material exiting the die cools so as to maintain its cross-sectional and longitudinal shape. The extruded material is the core.

In some embodiments, the extrude material may be captured in a bin or on a conveyor or manually by hand. In some embodiments, the extruded material may be feed into a cutting machine or may be manually cut at predetermined lengths to form the cores with the predetermined length. In some embodiments, the extruded material is not cut until after the injection molding process(es) (described below) is complete.

Next, the core is fed into a first injection molding machine. The mold of the injection molding machine is then closed, and the interdental section 102 including the fingers 134, 140, 142 are formed about a corresponding portion of the core by injecting a flowable material, such as heated thermoplastic elastomer (TPE), into the mold cavity or cavities. Then, the mold is allowed to cool. Then it is opened and/or the formed portion is ejected. Alternatively, the mold may be opened first then allowed to cool before the part is ejected.

Then, the core, including the portion with the interdental section 102 is advanced to a second injection molding machine where the handle and intermediate section are injection molded onto a corresponding portion of the core adjacent the interdental section 102. Then, the mold is opened and/or the interdental cleaner is ejected from the second injection molding machine. Then, the mold is allowed to cool. Then it is opened and/or the formed portion is ejected. Alternatively, the mold may be opened first then allowed to cool before the part is ejected.

The interdental section that is injection molded comprises thermoplastic elastomer. The handle and intermediate sections 103, 104 comprise polypropylene.

In another embodiment, after extruding the core 120 from the extruding machine, the core is fed into a two barrel injection molding machine that is capable of simultaneously, without opening the mold, injection molding (a) the interdental section with the fingers, and (b) the handle & intermediate sections, each comprising a different flowable material. In some embodiments, the two barrels may not be injected simultaneously but in series or in an overlapping sequence without opening the mold.

Then the mold is opened and/or the completed interdental cleaner is ejected from the two barrel injection molding machine. In another embodiment, a single barrel injection molding machine having an added external injection unit is used in place of a two barrel injection molding machine.

Figure 6:
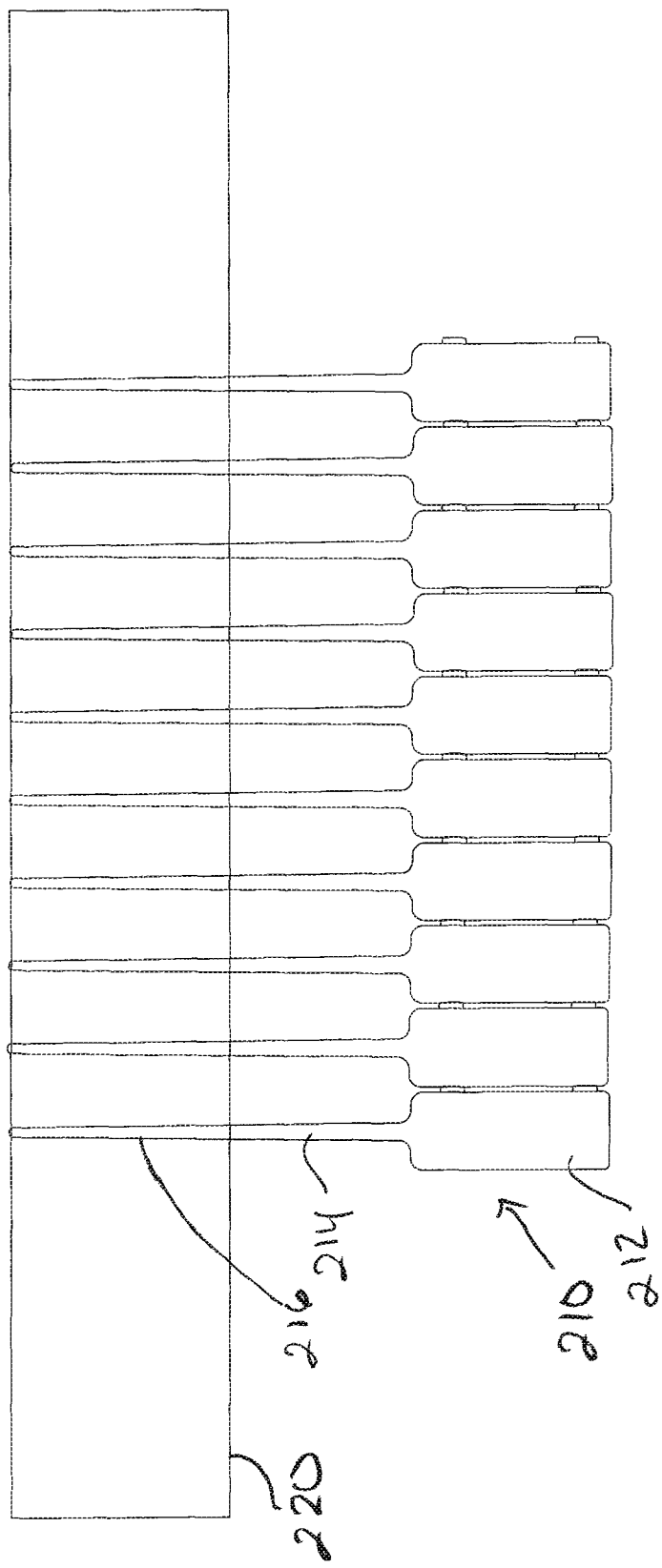
FIG. 6 is a front view of a plurality of second embodiment interdental cleaners at one stage of manufacturing

A second embodiment interdental cleaner 210 is shown in FIGS. 6-8. The cleaner 210 comprises a handle section 212 and a shaft section 214. At a proximal end 216 a cleaner element 230 is attached or formed with the proximal end 216 of the shaft section 214.

The cleaner element 230 may comprise nylon, cotton, polyester, or other woven fabric, or combination thereof. The handle and shaft section 212, 214 may each comprise a plastic such as polypropylene.

In some embodiments, the cleaner element has a degree of flexibility to accommodate being placed in an interdental space. Yet at the same time the cleaner element 230 will have a degree of stiffness to provide contact and cleaning to the tooth and gum tissue in and about the interdental spaces.

A manufacturing process and method is disclosed for forming the cleaner 210. First pull or put a strip 220 of cleaner material into an injection molding machine. In some embodiments, the strip is rectangular shape, but any other shape is also possible. The injection molding machine having a plurality of mold cavities capable of forming the plurality of cleaners 210, such as 10 cleaners shown in FIG. 6-7, simultaneously. The strip 210 extends across a plurality mold cavities corresponding to the plurality of cleaners desired. Before the mold is closed, material is heated until it is a flowable material. The mold is closed and the flowable material is injected into the mold cavities to form the handle section 212 and the shaft section 214. When the shaft section 214 is formed, flowable material will flow on both sides of the strip 220 to form the proximal end 216. As shown in FIG. 8, the strip 210 is laterally centered between a front face 216a and a back face 218b of the shaft 214. After the molding is complete, a plurality of cleaners 200 are removed from the mold.

The strip 220 is then cut about the shafts section 214 to form the cleaner element 230 on each of the cleaners 210, as shown in FIG. 7. This cutting step can be accomplished using a laser. In one embodiment, the plurality of cleaners 200 are held in a location and a computer controlled laser moves along a pre-programmed path to cut the shape of the cleaner element 230 about each cleaner 210. In some embodiments, a plurality of lasers corresponding to the plurality of cleaners 200 are used simultaneously so that each laser cuts a corresponding one of the cleaner elements 230 of the plurality of cleaners 200.

In some embodiments, the cutting step is performed by a stamping machine. The stamping machine utilizes a knife formed to cut each of the cleaning elements 230. The plurality of cleaners 200 with the strip 220 is held in place. Then a knife formed in an outline shape of the cleaner element 230 is lowered to cut about the proximal end 216 to form the cleaner element 230. In some embodiments, a plurality of knifes corresponding to the plurality of cleaners 200 are used simultaneously so that each knife cuts a corresponding one of the cleaner elements 230 of the plurality of cleaners 200. The shape of the cleaner element 230 are shown as trapezoidal, however, any other shape is also possible, such as square, quadrilateral, curved, irregular, oval, etc.

In another embodiment, one knife is used and it repeatedly makes a cutting motion to cut each of the plurality of cleaners 200. The knife may be mounted on a moving jig so that the knife moves according to a computer controlled motor to the next adjacent position to cut the next cleaning element 230 from the strip 220. In another embodiment, the machine provides a computer controlled base supporting the plurality of cleaners 200 and the base moves the plurality of cleaners after each cut until each of the cleaners 210 have been cut. In this arrangement the knife remains stationary.

The injection molding process forms bridges 214, 218 on at least one side of each handle section 212, which connect to the next adjacent cleaner 210. This allows all the cleaners 210 to be connected after exiting the mold. However the connection of the bridges 214, 218 to the adjacent cleaner is such that the bridges can be separated from the adjacent cleaner by applying a predetermined amount of force. Such force may be that exercised by a human hand so that a user can manually separate one cleaner from the next adjacent cleaner. Therefore the user can break off and use a cleaner until a new one is desired, while the unused new cleaners can remain joined together via the bridges. This allows the unused cleaners to be kept together for the convenience of storage.

While the method corresponding to FIGS. 6-8 is shown for making a plurality of cleaners in each molding process, one skilled in the art will recognize the process should also comprise one interdental cleaner mold for molding only one interdental cleaner per injection molding cycle.

In some embodiments, the injection molding machine is that described in U.S. Pat. No. 7,534,103, which is herein incorporated by reference. In some embodiments, the two barrel injection molding machine is a multi-cavity injection molding machine, such as disclosed in U.S. Pat. No. 5,223,275, which is herein incorporated by reference. In some embodiments, the extruding machine is that described in U.S. Pat. No. 3,300,811, which is herein incorporated by reference.

From the foregoing, it will be observed that numerous variations and modifications may be effected without departing from the spirit and scope of the invention. It is to be understood that no limitation with respect to the specific apparatus illustrated herein is intended or should be inferred.

The invention claimed is:

1. A method of manufacturing an interdental cleaner, comprising the steps of:
    feeding flowable nylon or polypropylene into a die;
    extruding the nylon or polypropylene out of an outer end of the die to form an elongated core having a solid cross-section;
    injection molding an interdental cleaner section, comprising a shaft and a plurality of fingers projecting from the shaft, from a thermoplastic elastomer about a first portion of the elongated core such that the elongated core extends longitudinally through the interdental cleaner section, the shaft and the plurality of fingers of the interdental cleaner section are formed by the injection molding; and,
    injection molding a handle portion from a polypropylene about a second portion of the elongated core such that the elongated core extends longitudinally through the handle portion.

2. The method of claim 1, further comprising the steps of feeding, before injection molding the interdental cleaner section, the first portion of the elongated core into a first injection molding machine;
    removing, after injection molding the interdental cleaner section, the interdental cleaner section and the elongated core from the first injection molding machine; and,
    placing, before injection molding the handle portion, at least the second portion of the elongated core in a second injection molding machine.

3. The method of claim 1, wherein the step of extruding comprises extruding the elongated core out of a circular outlet end of the die to form the elongated core in the shape of a cylindrical rod.

4. The method of claim 3, comprising the step of cutting the extruded cylindrical rod at a predetermined length to form the elongated core.

5. A method of manufacturing an interdental cleaner, comprising the steps of:
    feeding flowable nylon or polypropylene into a die;
    extruding an elongated core comprising nylon or polypropylene out of an outlet end of the die to form the elongated core, where the outlet end of the die imparts a final shape to the elongated core and wherein the elongated core comprises a solid cross section;
    feeding the elongated core into an injection molding machine;
    simultaneously injection molding
        an interdental cleaner section, comprising a shaft and a plurality of fingers projecting from the shaft, from a thermoplastic elastomer about a first portion of the elongated core such that the elongated core extends longitudinally through the interdental cleaner section, the shaft and the plurality of fingers of the interdental cleaner section are formed by the injection molding and,
        a handle portion from a polypropylene about a second portion of the elongated core.

6. The method of claim 5, wherein the step of extruding comprises extruding the elongated core out of a circular outlet end of the die to form the elongated core in the shape of a cylindrical rod.

7. The method of claim 6, comprising the step of cutting the extruded cylindrical rod at a predetermined length to form the elongated core.

8. The method of claim 5, wherein the step of extruding comprises the step of heating the nylon or polypropylene to a flowable state.

9. The method of claim 5, wherein the step of injection molding the interdental cleaner section is further defined in that the plurality of fingers are injection molded to form six rows of fingers, each row of fingers extends along a longitudinal length of the shaft of the interdental cleaner section, the six rows comprise a first row, a second row, a third row, a fourth row, a fifth row, and a sixth row, the first row is opposite of the second row, the third row and the fourth row are opposite the fifth row and the sixth row, the third row is adjacent the fourth row, and the fifth row is adjacent the sixth row.

10. The method of claim 9, wherein the step of injection molding the interdental cleaner section is further defined in that the fingers of the third row are vertically offset from the fingers of the fourth, the fingers of the fifth row are vertically offset from the fingers of the sixth row, the fingers of the first row are vertically offset from the fingers of the second row, the fingers of the third row, the fourth row, the fifth row, and the sixth row are vertically offset from the fingers of the second row, the fingers of the third row, the fourth row, the fifth row, and the sixth row are vertically offset from the fingers of the first row.

11. The method of claim 1, wherein the step of extruding comprises the step of heating the nylon or polypropylene to a flowable state.

12. The method of claim 1, wherein the step of injection molding the interdental cleaner section is further defined in that the plurality of fingers are injection molded to form six rows of fingers, each row of fingers extends along a longitudinal length of the shaft of the interdental cleaner section, the six rows comprise a first row, a second row, a third row, a fourth row, a fifth row, and a sixth row, the first row is opposite of the second row, the third row and the fourth row are opposite the fifth row and the sixth row, the third row is adjacent the fourth row, and the fifth row is adjacent the sixth row.

13. The method of claim 12, wherein the step of injection molding the interdental cleaner section is further defined in that the fingers of the third row are vertically offset from the fingers of the fourth, the fingers of the fifth row are vertically offset from the fingers of the sixth row, the fingers of the first row are vertically offset from the fingers of the second row, the fingers of the third row, the fourth row, the fifth row, and the sixth row are vertically offset from the fingers of the second row, the fingers of the third row, the fourth row, the fifth row, and the sixth row are vertically offset from the fingers of the first row.

14. The method of claim 1, comprising the steps of:
placing, before injection molding an interdental cleaner portion, the first portion of the elongated core into a first injection molding machine;
removing, after injection molding the interdental cleaner section, the interdental cleaner section and the elongated core from the first injection molding machine; and,
placing, after injection molding a handle portion, at least the second portion of the elongated core in a second injection molding machine;
wherein the step of extruding comprises the steps of
feeding flowable nylon or polypropylene into a die of an extruding machine, and
extruding the nylon or polypropylene out of an outlet end of the die from the elongated core.

15. A method of manufacturing an interdental cleaner, comprising the steps of:
feeding flowable nylon or polypropylene into a die of an extruding machine;
extruding the nylon or polypropylene out of an outlet end of the die to form an elongated core;
cutting the extruded elongated core at a predetermined length to form the elongated core with the predetermined length;
placing a first portion of the elongated core into a first injection molding machine;
injection molding an interdental cleaner section, comprising a shaft and a plurality of fingers projecting from the shaft, about a first portion of the elongated core, the interdental cleaner section comprising thermoplastic elastomer, the plurality of fingers of the interdental cleaner section are formed by the injection molding;
removing the formed interdental cleaner section and the elongated core from the first injection molding machine;
placing at least a second portion of the elongated core in a second injection molding machine; and,
injection molding a handle portion about the second portion of the elongated core, the handle portion comprising polypropylene.

* * * * *